(12) United States Patent
Brack

(10) Patent No.: US 7,101,401 B2
(45) Date of Patent: Sep. 5, 2006

(54) TIBIAL COMPONENT OF A KNEE-JOINT ENDOPROSTHESIS

(75) Inventor: René Brack, Cham (CH)

(73) Assignee: Plus Orthopedics AG, (CH)

( * ) Notice: Subject to any disclaimer, the term of this patent is extended or adjusted under 35 U.S.C. 154(b) by 26 days.

(21) Appl. No.: 10/337,922

(22) Filed: Jan. 7, 2003

(65) Prior Publication Data
US 2003/0153980 A1 Aug. 14, 2003

(30) Foreign Application Priority Data
Jan. 7, 2002 (DE) ............................... 102 00 263

(51) Int. Cl.
*A61F 2/38* (2006.01)
(52) U.S. Cl. .................................. 623/20.33
(58) Field of Classification Search .. 623/20.28–20.29, 623/20.32–20.33, 20.14, 20.15, 20.21
See application file for complete search history.

(56) References Cited

U.S. PATENT DOCUMENTS

| | | | |
|---|---|---|---|
| 3,824,630 A | | 7/1974 | Johnston |
| 5,683,468 A | * | 11/1997 | Pappas ..................... 623/20.29 |
| 5,755,801 A | * | 5/1998 | Walker et al. ........... 623/20.21 |
| 5,782,925 A | * | 7/1998 | Collazo et al. .......... 623/20.28 |
| 5,928,286 A | * | 7/1999 | Ashby et al. ............ 623/20.33 |
| 6,139,580 A | | 10/2000 | Wurzinger et al. |
| 6,210,444 B1 | | 4/2001 | Webster et al. |
| 6,217,618 B1 | | 4/2001 | Hileman |
| 6,238,434 B1 | | 5/2001 | Pappas |
| 6,296,666 B1 | * | 10/2001 | Gardner .................... 623/20.29 |
| 6,306,172 B1 | * | 10/2001 | O'Neil et al. ............. 623/20.15 |
| 6,319,283 B1 | | 11/2001 | Insall et al. |
| 6,361,564 B1 | * | 3/2002 | Marceaux et al. ........ 623/20.29 |
| 6,428,577 B1 | * | 8/2002 | Evans et al. ............. 623/20.29 |
| 6,491,726 B1 | | 12/2002 | Pappas |
| 6,558,427 B1 | | 5/2003 | Leclercq et al. |
| 6,623,526 B1 | * | 9/2003 | Lloyd ....................... 623/20.28 |
| 6,770,098 B1 | | 8/2004 | Hauri |

FOREIGN PATENT DOCUMENTS

| | | |
|---|---|---|
| EP | 0 634 155 A2 | 1/1995 |
| EP | 0 634 156 A2 | 1/1995 |
| GB | 2 304 051 A | 3/1997 |
| GB | 2 345 446 A | 7/2000 |

* cited by examiner

*Primary Examiner*—Bruce Snow
*Assistant Examiner*—Cheryl Miller
(74) *Attorney, Agent, or Firm*—Knobbe Martens Olson & Bear LLP

(57) ABSTRACT

Tibial component (10) of a knee-joint endoprosthesis with a flat tibial bearing surface (11), a bearing body (12) that is slidably seated thereon and comprises two concave bearing dishes (13) in which a femoral component can be movably seated, and with a rotational guide means that guides the rotation of the bearing body (12) on the tibial bearing surface (11) about an axis (14) perpendicular thereto. The guide means comprises a bearing post (15) in the form of a regular cylinder that stands upright on the tibial bearing surface (11) and has at least one projection (16, 17) extending radially outward. The bearing post so constructed can be inserted into a post receptacle (19) that is formed on the underside of the bearing body (12) with a receiving groove (20) corresponding to the post projection (16, 17). The at least one post projection (16, 17) extending radially outward is spaced apart from the free end (24) of the post.

9 Claims, 7 Drawing Sheets

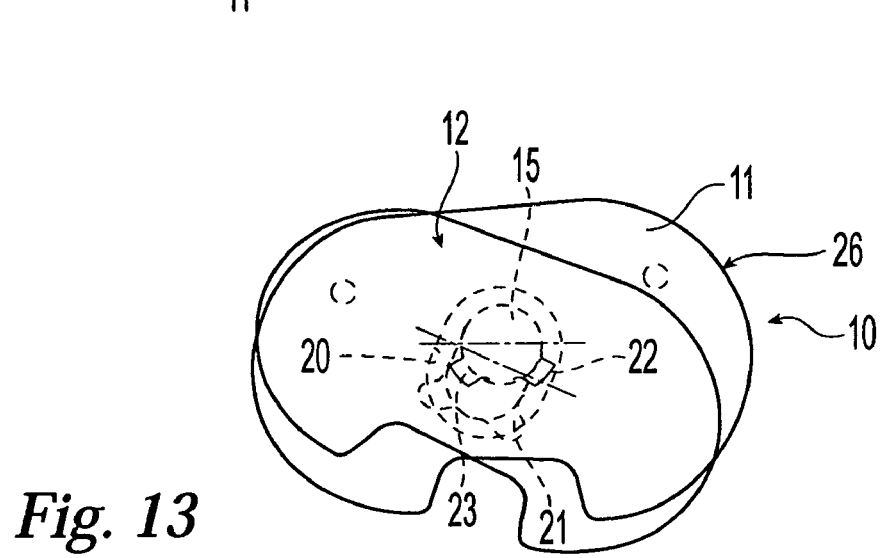
*Fig. 12*
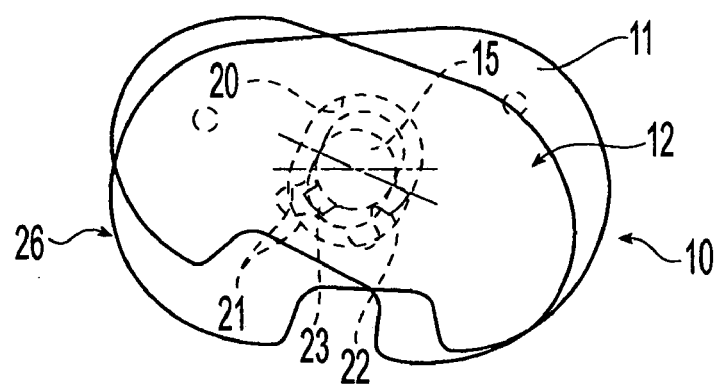
*Fig. 13*
*Fig. 14*

TIBIAL COMPONENT OF A KNEE-JOINT ENDOPROSTHESIS

FIELD OF THE INVENTION

The invention relates to a tibial component of a knee-joint endoprosthesis.

BACKGROUND OF THE INVENTION

A tibial component of this kind has been disclosed in the patents EP 0 864 306 A1 and WO 99/13804.

A feature common to these known tibial components is that on the exposed end face of the bearing post are disposed projections that extend radially outward. On the basis of this construction, to ensure that the only movement of the bearing body allowed on the associated tibial platform is rotational, it is necessary to provide a separate fixation screw as proposed in the document WO 99/13804; this prevents the translational movement of the bearing body on the tibial platform that is allowed in the original design. In the proposal according to WO 99/13804, so that the fixation screw can be screwed into the bearing post it must pass through the end face of the bearing body. Therefore, according to the state of the art, a separate component is needed to block translational movement, which makes the construction as a whole considerably more complicated and thus correspondingly more expensive. An additional disadvantage of the state of the art according to WO 99/13804 is that the fixation screw must pass through the bearing body, i.e., it must be screwed into the bearing post from the femoral side. This involves a not inconsiderable weakening of the bearing body. Furthermore, particles that have been detached by abrasion can migrate through the bearing body in both directions, from the tibial side to the femoral side and the reverse.

SUMMARY OF THE INVENTION

The present invention creates a tibial component of the kind cited above that gives the surgeon performing the operation the opportunity to make the bearing body capable only of rotation or, alternatively, capable of rotation as well as translation.

In accordance with the invention, in the otherwise smoothly cylindrical bearing post a post projection is provided that extends radially outward and is disposed at some distance from the free end of the post.

Thus, if the associated post receptacle on the underside of the bearing body is appropriately constructed, it is possible to determine whether the bearing post will allow only rotation on the tibial bearing surface or, alternatively, rotation as well as translation. No separate component is needed to limit the movement to rotation of the bearing body on the tibial bearing surface. All that is needed is that the cross-sectional area of the post receptacle be subdivided in such a way that the part that extends as far as the undercut region accommodating the post projection corresponds to the cross section of the opening, whereas the remainder of the receptacle has the configuration of a regular cylinder, corresponding to the contour of the cylindrical bearing post. The part with the latter cross section accommodates the part of the cylindrical bearing post that extends beyond the at least one radially outward-directed projection.

Preferably each of the post projections has a rod-like shape. However, they can also take the form of a flange or a discoid extension, in the latter case being shaped like a lunar crescent. At least two of the post projections are disposed so that they are either diametrically opposite one another, relative to the long axis of the post, or are set at a predetermined angle to one another, in particular an angle of about 90°.

To facilitate installation of the bearing body, the post receptacle in the bearing body has an opening with a cross section that corresponds to the cross-sectional contour of the bearing post including its projection or projections, i.e., the contour of the bearing post as seen in plan view from its end face. Hence the bearing post, including its projection(s), can be inserted into the post receptacle while in a predetermined rotational position with respect to bearing body and tibial bearing surface, to a distance such that when the bearing body is rotates on the tibial bearing surface into a relative initial position, the post projection(s) engage with the undercut section or groove formed in the post receptacle. The relative initial position between bearing body and tibial bearing surface is the position in which the bearing dishes on the femoral side of the bearing body are in the anterior/posterior orientation.

Preferably the at least one post projection is situated at about ⅔ of the total height of the bearing post. For example, if the bearing post is 8 mm long, the at least one radially outward-directed post projection will be situated about 5 mm above the tibial bearing surface. The height or thickness of the post projection(s) then amounts to about 1 mm, so that the post extends beyond the post-projection level by about 2 mm. An essential consideration for implementing the idea behind the invention is that the tibial component in accordance with the invention, can be combined with a bearing body, the post receptacle of which has a cross section that either corresponds throughout to that of the receptacle opening, or is altered along the length of the receptacle in such a way that up to the undercut or groove it corresponds to the opening cross section, but in the remainder it has a circular outline corresponding to the cross section of the cylindrical bearing post. The first of these alternatives allows the bearing body to be fixed onto the tibial sliding surface in such a way that the bearing body can be rotated thereon and also make translational back-and-forth movements. In its second embodiment, the bearing body can only be rotated on the tibial sliding surface, with no need for a separate component to block the translational movement.

An especially advantageous embodiment is distinguished by the fact that the post projection(s) extend in the anterior/posterior direction, whereas the long axis of the corresponding opening cross section of the post receptacle in the bearing body is oriented at an angle thereto, in particular an angle of about 45°. This embodiment makes it possible to position the bearing body on the receiving post without any major interference from the cruciate ligaments etc. At the same time, this arrangement provides great security against luxation of the bearing body, because in the normal case a rotation of the bearing body by 45°, i.e., into a position in which the bearing post could theoretically slide out of the associated receptacle opening, seems not to be possible.

In the extreme case, the receptacle opening on the underside of the bearing body extends transverse to the anterior/posterior axis, i.e., in a direction approximately parallel to the longitudinal extent of the bearing body, or medial/lateral. In this embodiment, however, the cruciate ligaments would be exposed to a not inconsiderable load when the bearing body is put into place, because when the bearing body is set onto the bearing post its long axis extends from posterior to anterior, i.e., transverse to the tibial sliding surface.

BRIEF DESCRIPTION OF THE DRAWINGS

In the following, preferred exemplary embodiments of a tibial component in accordance with the invention will be explained regarding their association with suitable bearing bodies, with reference to the attached drawings, wherein:

FIGS. 9–14 show another embodiment of a tibial component in plan view, to illustrate various positions of the bearing body relative to the component (tibial platform) that comprises the tibial bearing surface.

DETAILED DESCRIPTION OF THE INVENTION

Figure 1:
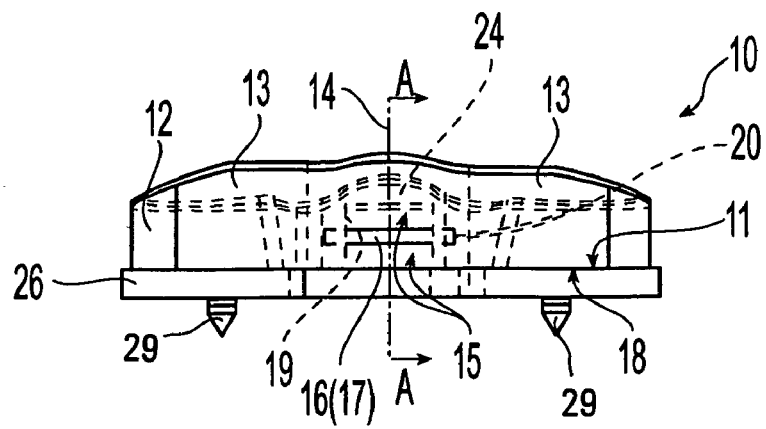
FIG. 1 shows a first embodiment of a tibial component in accordance with the invention as seen from the front.
Figure 2:
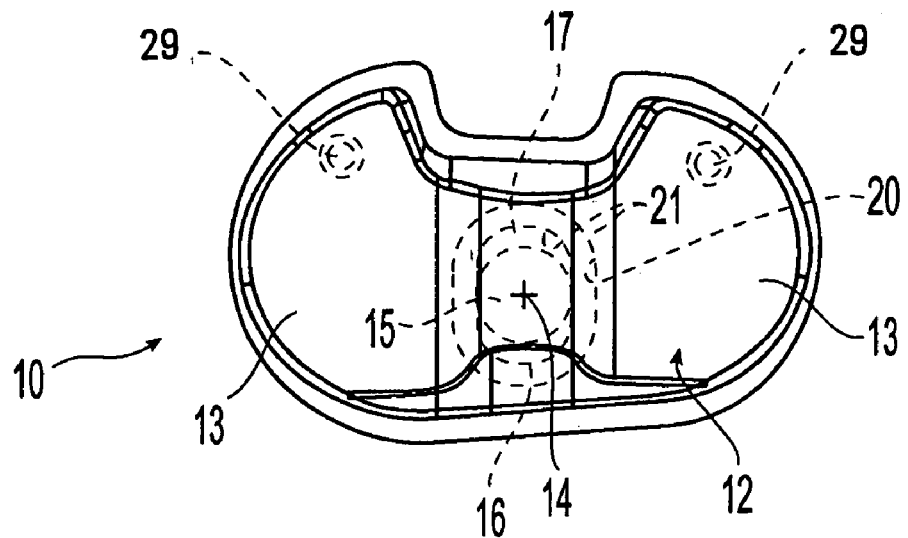
FIG. 2 shows the tibial component according to FIG. 1 in plan view.
Figure 3:
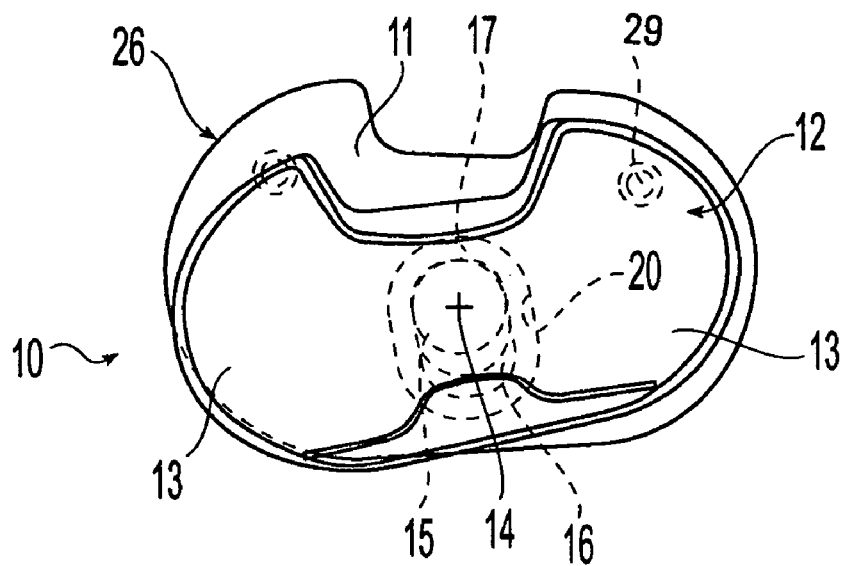
FIG. 3 shows the tibial component according to FIG. 1, again in plan view, but with the bearing body in a rotated position.

The embodiment of a tibial component 10 shown in FIGS. 1–3, which forms part of a knee-joint endoprosthesis, the other components of which are not shown here, defines a flat tibial bearing surface 11 on the femoral side of the associated component, the so-called tibial platform 26. A bearing body 12 made of a plastic compatible with human tissue, in particular polyethylene (PE), rests on and can slide over this tibial bearing surface. On the femoral side of the bearing body 12 are formed two concave bearing dishes 13, within which a femoral component can be movably seated. The tibial component shown here comprises a rotational guide means for the bearing body 12. This guide means ensures that the bearing body will be guided over the tibial bearing surface 11 about an axis of rotation 14 perpendicular to the latter, and consists of a cylindrical bearing post 15 oriented perpendicular to the tibial bearing surface 11 and comprising two projections 16, 17, each of which extends radially outward. The bearing post 15 so constructed can be positioned by inserting the post projections 16, 17 into a circumferential groove 20 within the sliding surface 18 of the bearing body 12 that is turned towards the tibial bearing surface 11, or into a post receptacle 19 formed in the underside of the latter. Each of the post projections 16, 17 is a flat structure in the shape of a lunar crescent, and extends diametrically, with respect to the post long axis, in the posterior or anterior direction. The post long axis defines the above-mentioned axis of rotation 14 of the bearing body 12.

Figure 1A:
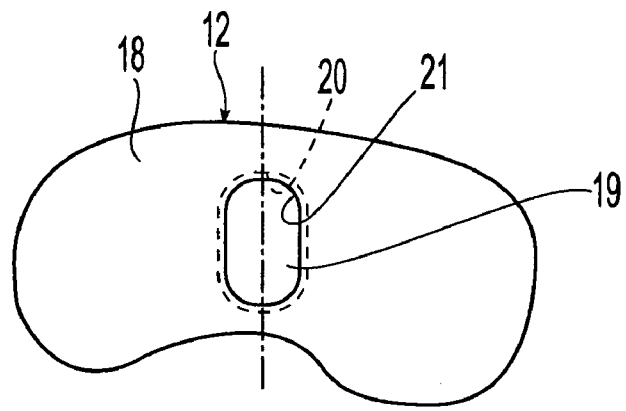
FIG. 1a shows the bearing body according to FIG. 1 as seen from below.
Figure 1B:
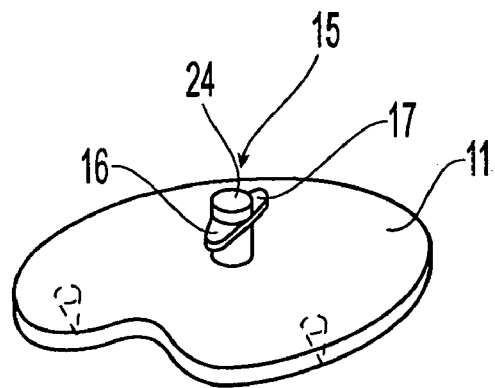
FIG. 1b shows the part of the tibial component shown in FIG. 1 that includes the bearing post (i.e., the tibial platform), in perspective from diagonally above.
Figure 7:
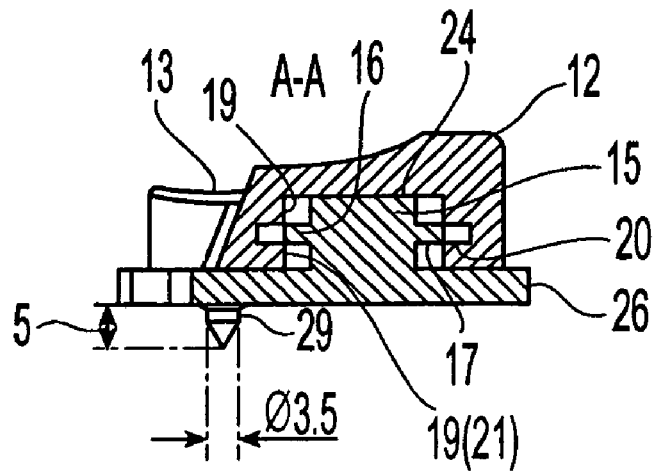
FIG. 7 shows a section through the tibial component according to FIG. 1, along the line A—A.
Figure 8:
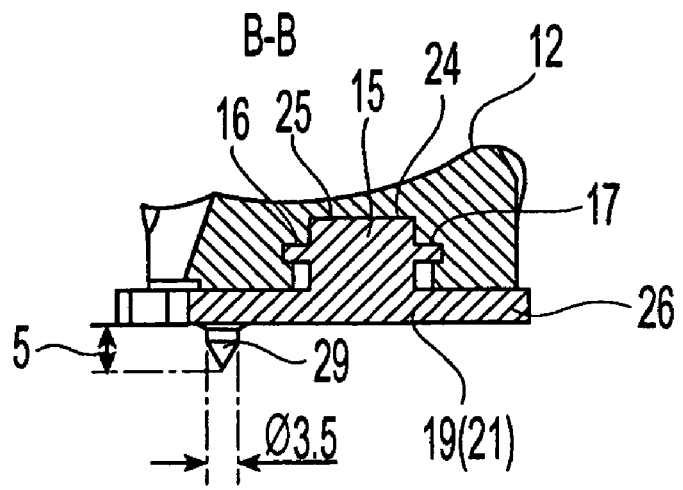
FIG. 8 shows a section through the tibial component according to FIG. 4, along the line B—B.

As shown especially clearly in FIGS. 1b and 7, the bases of the post projections 16, 17 are situated at a predetermined distance from the free end 24 of the post. They are positioned at a level corresponding to about ⅔ of the overall height of the bearing post 15.

The opening of the post receptacle 19 in the bearing body 12 has a cross-sectional configuration 21 corresponding to the elongated oval cross section of the bearing post 15 including its projections 16, 17, so that the bearing post with its projections can be inserted into the post receptacle only when the bearing body is in certain predetermined rotational positions with respect to the tibial bearing surface or tibial platform, and only for a distance such that the post projections engage with the groove 20 formed in the post receptacle 19 when the bearing body is rotated on the tibial bearing surface 11. This engagement of the post projections 16, 17 in the circumferential groove 20 within the post receptacle 19 is particularly clearly illustrated in FIG. 3. As shown in FIGS. 1a and 2, the oval opening of the post receptacle 19 extends in the anterior/posterior direction. Because the projections 16, 17 on the post 15 also extend anteroposteriorly, the bearing body 12 can be set onto the bearing post 15 with projections 16, 17 while in a corresponding relative orientation, shown in FIG. 2. Hence when the bearing body 12 is being put into place, care must be taken to ensure that the oval opening of the post receptacle 19 is likewise anteroposteriorly oriented.

As can very clearly be seen in FIGS. 2 and 3, the embodiment of a tibial component described here is distinguished by the fact that the bearing body 12 is seated on the tibial bearing surface 11 so as to be capable of both rotational and translational movement.

Figure 6:
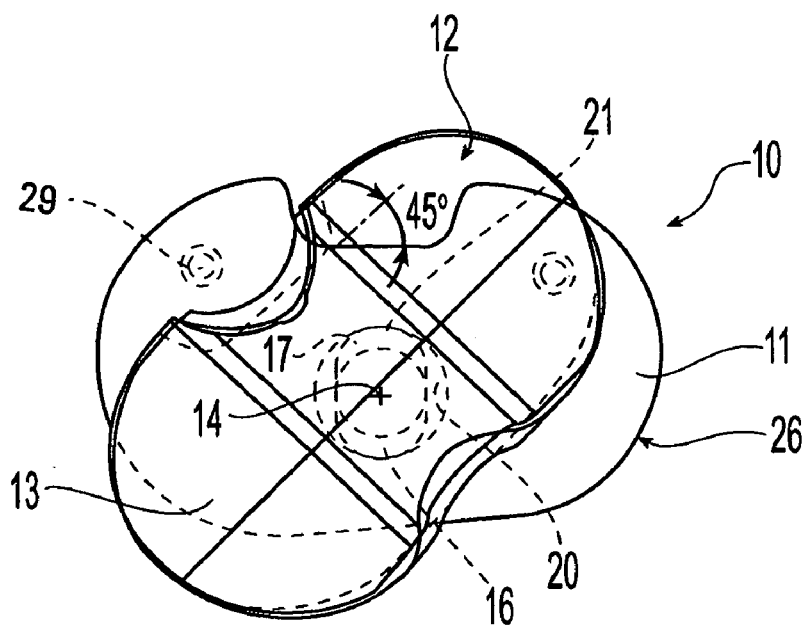
FIG. 6 shows the tibial component according to FIG. 4 in plan view with the bearing body rotated by 45°, in a position such that the bearing body can be pushed onto or pulled away from the bearing peg.

To prevent the bearing body 12 from unintentionally being lifted up from the tibial bearing surface 11 when the bearing body 12 is in its normal position, shown in FIG. 2, it is advantageous for the oval opening of the post receptacle 19 on the underside of the bearing body 12 to extend at an angle to the anterior/posterior extent of the associated post projections 16, 17, as is the case in the exemplary embodiment according to FIGS. 4–6 and 8. As can be seen in FIG. 6, the post projections 16, 17 extend anteroposteriorly just as in the embodiment according to FIGS. 1–3 and 7, whereas the corresponding oval opening cross section 21 of the post receptacle 19 in the bearing body 12 extends at an angle β thereto amounting to 45°. For this reason, it is possible for the bearing body 12 to be mounted on the tibial platform 26 only when the bearing body is in this 45° position relative to the tibial bearing surface 11 and the tibial platform 26, as shown in FIG. 6. When the bearing body 12 is rotated back into the normal position shown in FIG. 5, the post projections 16, 17 engage the circumferential groove 20 within the post receptacle 19. In the embodiment according to FIGS. 4–6 and 8 the circumferential groove 20 formed within the post receptacle 19 has a circular shape, whereas in the first exemplary embodiment it conforms to the contour of the oval opening cross section 21 of the post receptacle 19. The circular groove corresponding to FIGS. 4–6 and 8 is technically simpler to construct than the oval groove provided in the first exemplary embodiment.

The second embodiment, in which identical parts are identified by the same reference numerals as in the first embodiment, is also distinguished from the first embodiment in particular by the subdivision of the post receptacle 19 so that it has two cross-sectional configurations. As far along its length as the groove 20 to receive the post projection, the post receptacle has a cross section corresponding to that of the opening 21. The remaining cross section 25 of the post receptacle 19 has the shape of a regular cylinder and thus corresponds to the cross section of the cylindrical bearing post 15. Accordingly, the part of the bearing post 15 that extends beyond the bearing projections 16, 17 can be fitted into this latter cross section in such a way that movement of the bearing body 12 is restricted to rotation.

The tibial platform in both embodiments is further characterized by comprising on its underside two bone-fixation thorns 29, situated near the posterior limit of the tibial platform 26.

The post 15 is made integral with the tibial platform 26. In principle, however, it is also conceivable to construct the bearing post 15 as a separate component and attach it to the tibial platform 26 by means of a fixation screw.

Figure 4:
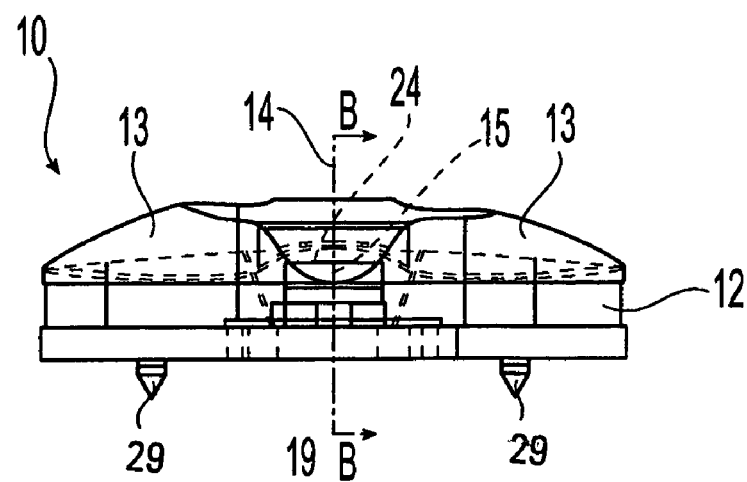
FIG. 4 shows a second embodiment of a tibial component in accordance with the invention as seen from the front.
Figure 4A:
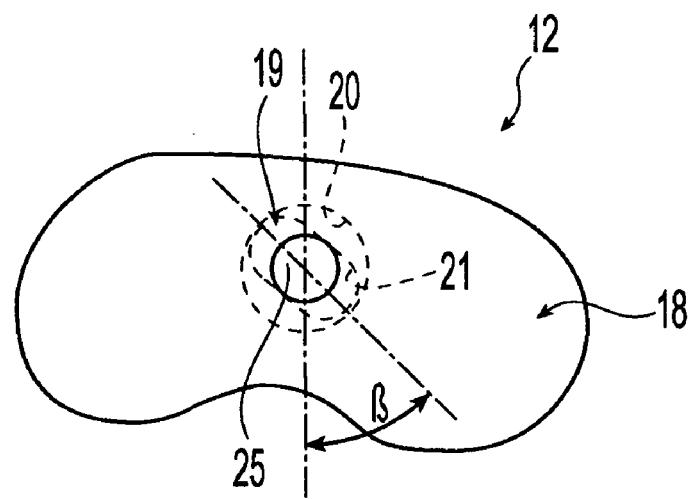
FIG. 4a shows the bearing body as seen from below.
Figure 5:
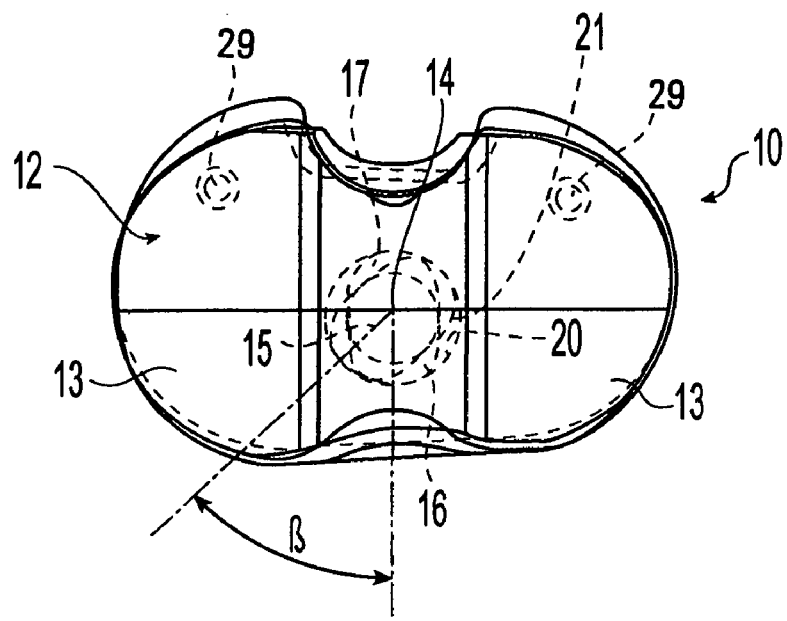
FIG. 5 shows the tibial component according to FIG. 4 in plan view.

Regarding the second-exemplary embodiment, special reference is also made to FIG. 4a, a view of the bearing body 12 from below to show its slide face 18 on the tibial side. The orientation of the oval opening 21 of the post receptacle 19 is clearly visible, as is the circular groove 20 to receive the post projections. The circular cross section 25 corresponding to the cross section of the cylindrical bearing post 15 in the lower floor region of the post receptacle 19 is also clearly evident here. This cylindrical cross section 25 ensures that movement of the bearing body 12 is restricted to rotation about the post 15, i.e., about its long axis 14.

In the third embodiment, shown in FIGS. 9 to 14, again identical parts are identified by the same reference numerals as for the preceding embodiments. Hence the description of these parts will not be repeated here; instead, reference is made to the description of the first two embodiments.

Figure 10:
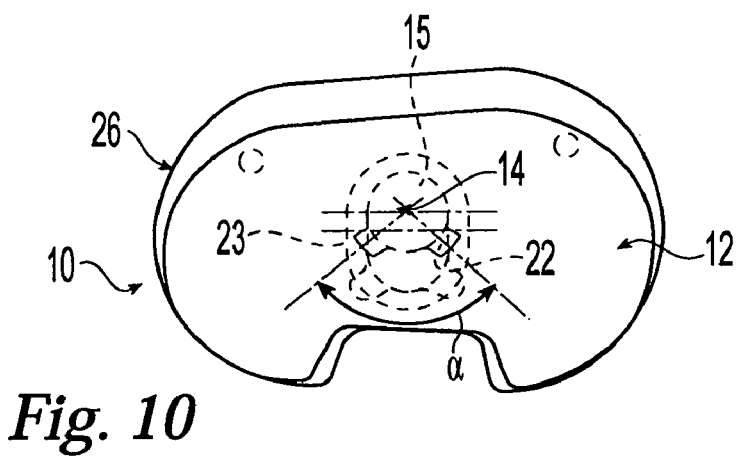

The third embodiment is characterized in particular by the fact that the bearing post 15 comprises two rod-like projections 22, 23, positioned at a predetermined angle a to one another, in this case about 100° (see FIG. 10).

Figure 9:
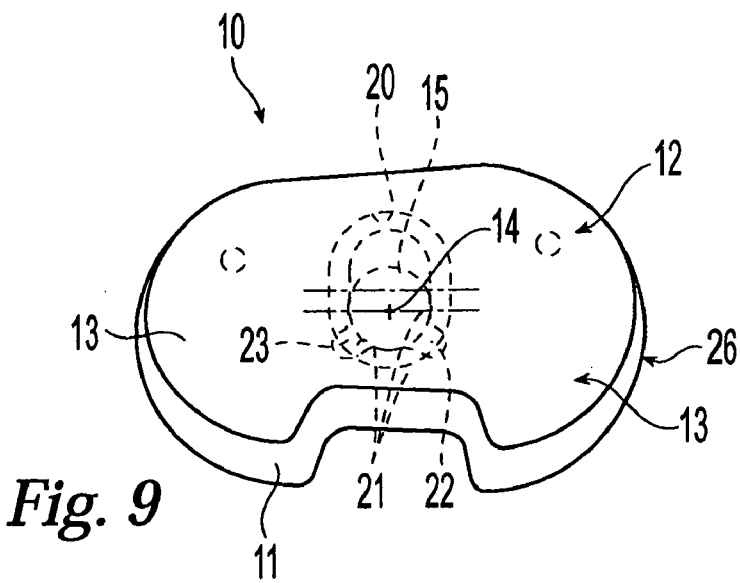
Figure 11:
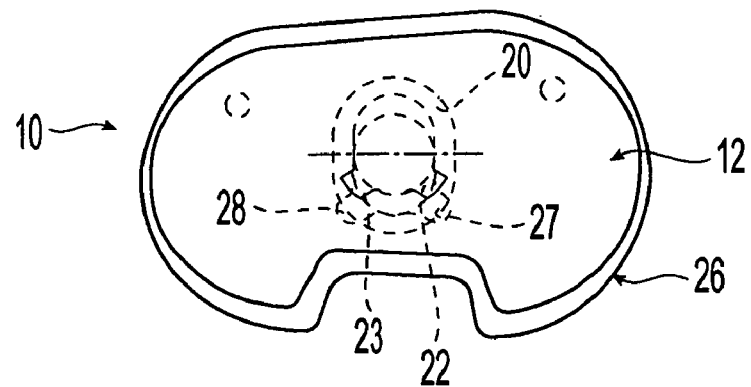

To accommodate these projections the opening cross section 21 of the post receptacle 19 in the bearing body 12 must comprise cut-out sections, which for example in FIG. 11 are identified by the reference numerals 27, 28. When these recesses 27, 28 are appropriately positioned with respect to the rod- or lug-like projections 22, 23, the bearing body 12 can be set onto the bearing post 15. This position of the bearing body 12 relative to the tibial bearing surface 11 or tibial platform 26 is shown in FIG. 9.

All the other FIGS. 10 to 14 show different relative positions of bearing post 15, with projections 22, 23, and bearing body 12. It is evident that in all these other relative positions the post projections 22, 23 extend into the oval circumferential groove 20 within the post receptacle 19 and thereby prevent the bearing body 12 from being lifted away from the tibial platform 26.

In the embodiment shown here, the lug- or rod-like post projections 22, 23 are directed posteriorly. It is equally conceivable for them to aim in any other direction. In practice, however, the orientation of the post projections 22, 23 has proved useful in that after the bearing body 12 has been set into place in a position corresponding to FIG. 9, anatomical factors cause it to shift into a position in which the post projections 22, 23 engage the associated receptacle groove 20, i.e., at least into a position corresponding to FIG. 11. With only a slight rotation of the bearing body 12, the above-mentioned engagement of at least one of the two post projections 22, 23 with the circumferential groove 20 likewise occurs, as can be seen in FIGS. 12 to 14. In all these cases the bearing body 20 is securely retained on the tibial bearing surface 11, and hence on the tibial platform 26.

In the embodiment according to FIGS. 9 to 14, again, it is conceivable to construct the post receptacle 19 so that it has two parts with different cross sections; that is, the part of the post receptacle 19 at the bottom can have a cross-sectional configuration in the form of a regular cylinder, corresponding to the cylindrical shape of the bearing post 15. Then the part of the bearing post 15 that extends beyond the post projections 22, 23 engages this cylindrical opening.

The tibial platform, together with the bearing post, is made in the conventional manner of a material compatible with human tissue, in particular a titanium alloy.

All the characteristics disclosed in the application documents are claimed as essential to the invention insofar as they are new to the state of the art individually or in combination.

List of Reference Numerals

10 Tibial component
11 Tibial bearing surface
12 Bearing body
13 Bearing dish
14 Axis of rotation
15 Bearing post
16 Radial projection
17 Radial projection
18 Slide face or underside of bearing body
19 Post receptacle
20 Groove to receive post projection
21 Opening cross section
22 Radial projection
23 Radial projection
24 Free end of post
25 Cross section
26 Tibial platform
27 Recess in opening cross section
28 Recess in opening cross section
29 Bone-fixation thorn

What is claimed is:

1. A tibial component of a knee-joint endoprosthesis, the tibial component comprising a flat tibial bearing surface, a bearing body that is slidably seated thereon and comprises two concave bearing dishes in which a femoral component can be movably seated, and a rotational guide that guides the rotation of the bearing body on the tibial bearing surface about an axis perpendicular thereto, wherein the guide comprises a bearing post in the form of a regular cylinder that stands upright on the tibial bearing surface and terminates at a free end, the guide further comprising first and second elongate post projections extending radially outward from the cylinder, the guide comprising a cylindrical section above the post projections, the post projections being spaced from the free end of the cylinder by a first distance, the post projections also being spaced above the tibial bearing surface by a first height, wherein the first and second post projections comprise longitudinal axes lying along a single line which is substantially parallel to an anterior-posterior axis, the guide configured to be inserted into a post receptacle on a slide face on a side of the bearing body facing the tibial bearing surface, the post receptacle further comprising a recess or groove corresponding to a height of the post projections, the post receptacle having an elongate opening sized to receive the guide and post projections, the opening having a longitudinal axis along a major axis of the opening transverse to a minor axis of the opening, wherein the longitudinal axis of the opening lies at a non-zero angle with respect to both an anterior-posterior axis and a medial-lateral axis of the bearing body.

2. The tibial component according to claim 1, wherein the post projections are constructed in a flange or disklike shape.

3. The tibial component according to claim 2, wherein the post projections are disk-like in structure, having the shape of a lunar crescent.

4. The tibial component according to claim 1, wherein the post receptacle in the bearing body comprises an opening with a cross section corresponding in shape to the cross-sectional configuration of the bearing post with the post projections, so that when the bearing body is turned into a predetermined orientation with respect to the tibial bearing surface, the bearing post and post projections can be inserted into the post receptacle far enough to place the post projections at the level of the recess or groove formed in the post receptacle to receive the post projections, so as to permit engagement therewith.

5. The tibial component according to claim 1, wherein the post projections are disk-like in structure, having the shape of a lunar crescent.

6. The tibial component according to claim 1, wherein the first height of the post projections is situated at a level corresponding to about ⅔ of an overall height of the bearing post.

7. The tibial component according to claim 1, wherein the longitudinal axis of the opening lies at an angle of about 45 degrees with respect to an anterior-posterior axis of the bearing body.

8. The tibial component according to claim 1, wherein the recess or groove to receive the post projections either conforms to the contour of the cross section of the post receptacle or is circular with an inside diameter corresponding to the maximum extent of the opening cross section of the post receptacle.

9. The tibial component according to claim 1, wherein the post receptacle comprises a cross section differing at different depths in the receptacle, a first cross-section corresponding to a shape of the opening and extending between the bottom slide face and the recess, and a second cross-section comprising a shape of a regular cylinder and located above the first cross-section, the second cross-section corresponding to the cross section of the cylindrical bearing post.

* * * * *

UNITED STATES PATENT AND TRADEMARK OFFICE
CERTIFICATE OF CORRECTION

| | | |
|---|---|---|
| PATENT NO. | : 7,101,401 B2 | Page 1 of 1 |
| APPLICATION NO. | : 10/337922 | |
| DATED | : September 5, 2006 | |
| INVENTOR(S) | : Rene Brack | |

It is certified that error appears in the above-identified patent and that said Letters Patent is hereby corrected as shown below:

At Col. 5, Line 15, delete "secondary-exemplary" and insert--second exemplary--, therefor.

At Col. 5, Line 33, after "angle" delete "a" and insert -- $\alpha$ -- , therefor.

At Col. 5, Line 40, delete "lug-like" and insert -- lug- like --, therefor.

Signed and Sealed this

Eighth Day of May, 2007

JON W. DUDAS
*Director of the United States Patent and Trademark Office*